United States Patent
Guo et al.

(10) Patent No.: US 12,327,348 B2
(45) Date of Patent: Jun. 10, 2025

(54) OPERATING METHOD OF MEDICAL IMAGING SYSTEM AND MEDICAL IMAGING SYSTEM

(71) Applicant: GE Precision Healthcare LLC, Wauwatosa, WI (US)

(72) Inventors: Zhaohua Guo, Beijing (CN); Yong Xu, Beijing (CN); Ziyi Yuan, Chengdu (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 539 days.

(21) Appl. No.: 17/647,626

(22) Filed: Jan. 11, 2022

(65) Prior Publication Data
US 2022/0230309 A1    Jul. 21, 2022

(30) Foreign Application Priority Data
Jan. 15, 2021  (CN) .................. 202110055974.X (51) Int. Cl.
  G06T 7/00   (2017.01)
  G06T 7/11   (2017.01)
  G06V 10/25  (2022.01)
  G06V 10/94  (2022.01)

(52) U.S. Cl.
  CPC .............. G06T 7/0012 (2013.01); G06T 7/11 (2017.01); G06V 10/25 (2022.01); G06V 10/945 (2022.01); *G06T 2207/10116* (2013.01)

(58) Field of Classification Search
  CPC ............. G06T 5/50; G06T 2207/20084; G06T 2207/20208; G06T 2207/10144; G06T 2207/20081; G06T 2207/10016; G06T 2207/10024; G06T 2207/20221; G06T 5/60; G06T 5/92; G06T 7/11; G06T 15/506; G06T 19/006; G06T 2200/24; G06T 2207/10152; G06T 2210/04; G06T 5/77; G06T 7/194; G06T 7/70
  USPC ........................................... 382/128
  See application file for complete search history.

(56) References Cited

U.S. PATENT DOCUMENTS

2021/0271837 A1*  9/2021  Kawashima ....... G06K 7/10752
2022/0110602 A1*  4/2022  Shang .................... A61B 6/542

FOREIGN PATENT DOCUMENTS

CN  107049344 A   8/2017
CN  107320119 B   12/2020
WO  2012161470 A2  11/2012

OTHER PUBLICATIONS

EP application 22150018.4 filed Jan. 3, 2022—extended Search Report issued May 11, 2022; 7 pages.
WO2012161470—English Translation from TXPMTEA; 15 pages.
CN application 202110055974.X filed Jan. 15, 2021—Office Action issued Sep. 13, 2024; 8 pages.
CN107049344 English Abstract, obtained from Espacenet.com Dec. 11, 2024; 1 page.
CN107320119 English Abstract, obtained from Espacenet. com Dec. 11, 2024; 1 page.

* cited by examiner

*Primary Examiner* — Ajibola A Akinyemi (57) ABSTRACT

Provided in the present application are an operating method of a medical imaging system and a medical imaging system. The operating method of the medical imaging system includes performing exposure setting of a next object during image processing of medical image data of a current object.

16 Claims, 9 Drawing Sheets

OPERATING METHOD OF MEDICAL IMAGING SYSTEM AND MEDICAL IMAGING SYSTEM

CROSS REFERENCE

The present application claims priority and benefit of Chinese Patent Application No. 202110055974.X filed on Jan. 15, 2021, which in incorporated herein by reference in its entirety.

FIELD OF THE INVENTION

The present invention relates to medical imaging technology, and more specifically to an operating method of a medical imaging system and a medical imaging system.

BACKGROUND OF THE INVENTION

In an X-ray imaging system, radiation from an X-ray source is emitted toward a subject, and the object under examination is usually a patient in a medical diagnosis application. A part of the radiation passes through the object under examination and impacts a detector, which is divided into a matrix of discrete elements (e.g., pixels). The detector elements are read to generate an output signal on the basis of the amount or intensity of radiation that impacts each pixel region. The signal can then be processed to generate a medical image that can be displayed for review, and the medical image can be displayed in a display device of the X-ray imaging system.

For an examination process of an object to be examined, it is usually necessary to perform pre-exposure preparations such as protocol selection and positioning on a control terminal in a scan room. Afterwards, the object to be examined is exposed. Upon completion of the exposure, data will be transferred to a control terminal in a control room outside the scan room, and then post-processing and other operations on an acquired medical image. Scan examination of a next object to be examined will not start before the post-processing process ends. Such a procedure setting will increase the examination time and reduce the scanning efficiency.

BRIEF DESCRIPTION OF THE INVENTION

Provided in the present invention are an operating method of a medical imaging system and a medical imaging system.

Provided in an exemplary embodiment of the present invention is an operating method of a medical imaging system. The operating method comprises performing exposure setting of a next object during image processing of medical image data of a current object.

Specifically, the performing exposure setting of a next object comprises performing the exposure setting of the next object on the basis of estimated time required for the image processing.

Specifically, estimating the time required for the image processing comprises estimating the required time on the basis of an imaging protocol of the current object.

Specifically, when the time required for the image processing is less than a first threshold, the exposure setting of the next object is performed.

Specifically, when the time required for the image processing is greater than a second threshold, an instruction signal is generated to stop examination of a subsequent object.

Specifically, before the performing exposure setting of a next object, the method further comprises: selecting the next object in an object list on the basis of an imaging protocol of each object according to the estimated time required for the image processing.

Specifically, the operating method further comprises: starting to perform exposure on the next object after the image processing process of the current object and the exposure setting for the next object are complete.

Specifically, performing the image processing on the medical image data of the current object comprises displaying an interface for the image processing by a first display module, and the exposure setting of the next object comprises displaying an interface for the exposure setting by a second display module, and the operating method further comprises: after the image processing process of the current object is complete, synchronizing the interface for the exposure setting to the first display module for display.

Specifically, the exposure setting comprises at least one of selection in an object list, confirmation of object information, selection of a protocol, and positioning.

Further provided in an exemplary embodiment of the present invention is a non-transitory computer-readable storage medium for storing a computer program, wherein when executed by a computer, the computer program causes the computer to perform the operating method described above.

Further provided in an exemplary embodiment of the present invention is a medical imaging system. The medical imaging system comprises a first user module, a second user module, and a control module, wherein the first user module is configured to perform image processing on an acquired medical image, the second user module is configured to perform exposure setting, and the control module is configured to perform exposure setting of a next object via the second user module during image processing of medical image data of a current object by the first user module.

Specifically, the first user module is located in a control room, and the second user module is located in a scan room.

Specifically, the first user module comprises an interface for displaying the image processing, the second user module comprises an interface for the exposure setting, and the first user module is configured to synchronously display the interface for the exposure setting of the next object displayed by the second user module when the image processing process of the current object ends.

Specifically, at least one of the first user module and the second user module is further configured to perform an exposure operation after the image processing process of the current object and the exposure setting of the next object are complete.

Specifically, the control module is further configured to perform, during the image processing of the medical image data of the current object by the first user module, the exposure setting of the next object via the second user module on the basis of estimated time required for the image processing. Further, when the time required for the image processing is less than a first threshold, the exposure setting of the next object is performed.

Specifically, the control module is further configured to generate an instruction signal to stop examination of a subsequent object on the basis of the time required for the image processing.

Specifically, the control module is further configured to select the next object in an object list on the basis of an imaging protocol of each object according to the estimated time required for the image processing.

Further provided in an exemplary embodiment of the present invention is a medical imaging system. The medical imaging system comprises a first user module, at least one second user module, and a control module, wherein the first user module is configured to perform image processing on an acquired medical image, the at least one second user module is respectively configured to perform exposure setting on different objects, and the control module is configured to perform exposure setting on the different objects via the second user module during image processing of medical image data of a current object by the first user module.

Specifically, the first user module is located in a control room, and the at least one second user module is located in a scan room.

Specifically, the first user module comprises an interface for displaying the image processing, the second user module comprises an interface for the exposure setting, and the first user module is configured to synchronously display the interface for the exposure setting of the next object displayed by the second user module when the image processing process of the current object ends.

Specifically, at least one of the first user module and the second user module is further configured to perform an exposure operation after the image processing process of the current object and the exposure setting of the next object are complete.

Specifically, the control module is further configured to perform, during the image processing of the medical image data of the current object by the first user module, the exposure setting of the next object via the second user module on the basis of estimated time required for the image processing. Further, when the time required for the image processing is less than a first threshold, the exposure setting of the next object is performed.

Specifically, the control module is further configured to generate an instruction signal to stop examination of a subsequent object on the basis of the time required for the image processing.

Specifically, the control module is further configured to select the next object in an object list on the basis of an imaging protocol of each object according to the estimated time required for the image processing.

Other features and aspects will become clear through the following detailed description and accompanying drawings.

BRIEF DESCRIPTION OF THE DRAWINGS

The present invention may be better understood by means of the description of exemplary embodiments of the present invention with reference to accompanying drawings, in which.

DETAILED DESCRIPTION

Specific implementations of the present invention will be described in the following. It should be noted that during the specific description of the implementations, it is impossible to describe all features of the actual implementations in detail in this description for the sake of brief description. It should be understood that in the actual implementation of any of the implementations, as in the process of any engineering project or design project, a variety of specific decisions are often made in order to achieve the developer's specific objectives and meet system-related or business-related restrictions, which will vary from one implementation to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The terms "first," "second," and similar terms used in the description and claims of the patent application of the present invention do not denote any order, quantity, or importance, but are merely intended to distinguish between different constituents. The term "one", "a(n)", or a similar term is not meant to be limiting, but rather denote the presence of at least one. The term "include", "comprise", or a similar term is intended to mean that an element or article that appears before "include" or "comprise" encompasses an element or article and equivalent elements that are listed after "include" or "comprise", and does not exclude other elements or articles. The term "connect", "connected", or a similar term is not limited to a physical or mechanical connection, and is not limited to a direct or indirect connection.

Figure 1:
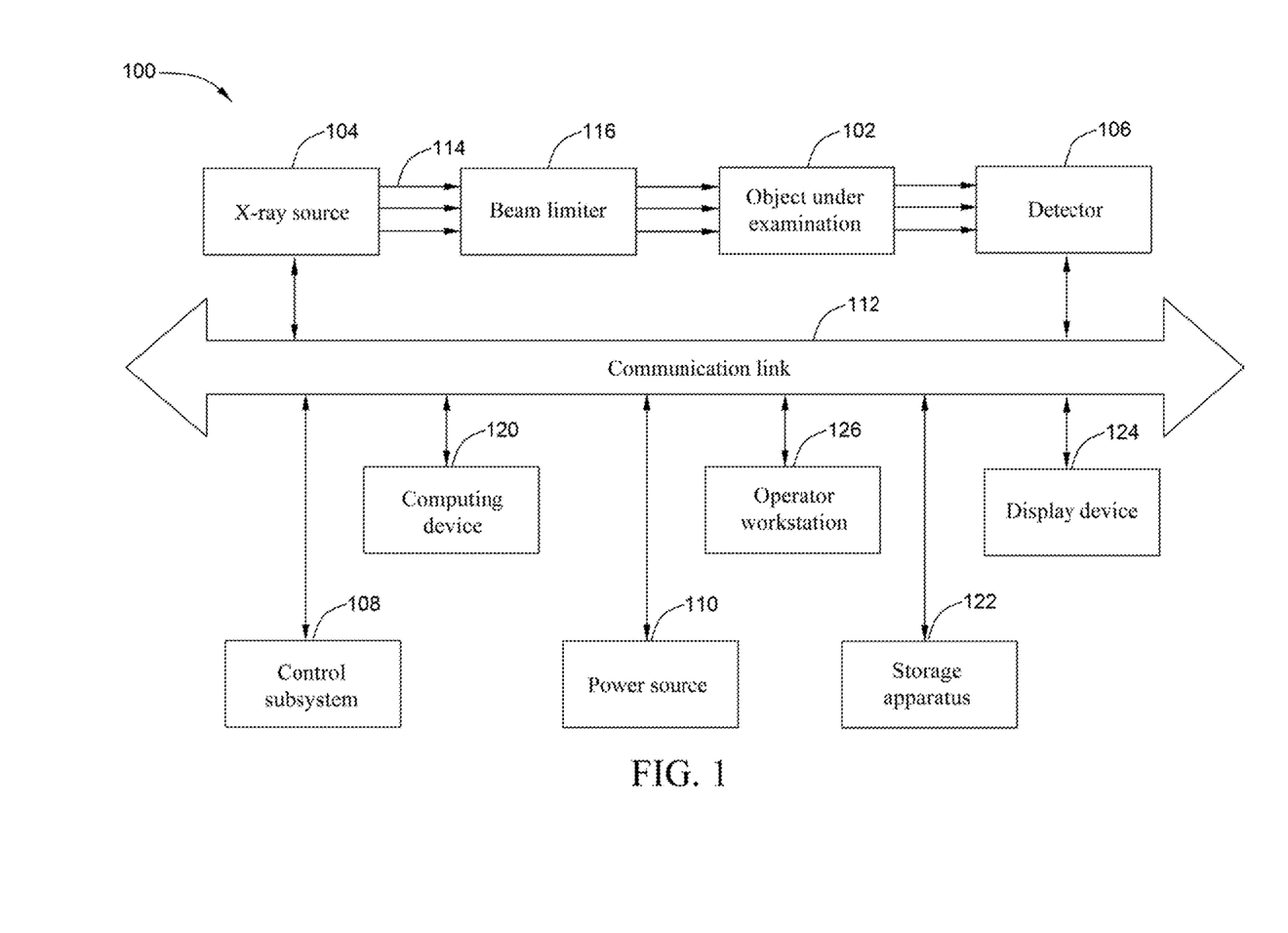
FIG. 1 is a schematic diagram of an X-ray imaging system according to some embodiments of the present invention.

FIG. 1 shows an X-ray imaging system 100 according to some embodiments of the present invention. As shown in FIG. 1, the X-ray imaging system 100 includes an X-ray source 104, a detector 106, and a control subsystem 108. In some embodiments, the X-ray imaging system 100 may be a fixed X-ray imaging system disposed in a fixed X-ray imaging room, or may be a mobile X-ray imaging system.

The X-ray source 104 can project X-rays 114 onto an expected region of interest in an object under examination 102. Specifically, the X-ray source 104 may be positioned adjacent to a beam limiter 116, and the beam limiter 116 is configured to align the X-rays 114 to the expected region of interest in the object under examination 102. At least part of the X-rays 114 may be attenuated through the object under examination 102 and may be incident on the detector 106.

The control subsystem 108 includes a source controller (not shown in the figure) and a detector controller (not shown in the figure). The source controller is configured to instruct the X-ray source 104 to emit X-rays 114 for image exposure. The detector controller is configured to coordinate control of various detector functions, such as executing various signal processing and filtering functions, specifically, configured to perform initial adjustment of a dynamic range, interleaving of digital image data, and the like. In some embodiments, the control subsystem 108 may provide power and timing signals for controlling the operation of the X-ray source 104 and the detector 106. Exactly speaking, the control subsystem 108 may provide power and timing signals to the X-ray source 104 and/or the detector 106 by using a power source 110 and one or a plurality of wired and/or wireless communication links 112, respectively, wherein the communication link 112 may correspond to a backplane bus, a local area network, a wide area network, and/or the Internet. In some embodiments, the power source 110 includes one or a plurality of batteries. In addition, although FIG. 1 shows that the power source 110 is connected to the X-ray source 104 through the communication link, those skilled in the art should understand that the power source 110 may also be directly coupled to the X-ray source 104.

The control subsystem 108 may be configured and/or arranged for use in different manners. For example, in some implementations, a single control subsystem 108 may be used. In other implementations, a plurality of control subsystems 108 are configured to work together (for example, configured based on distributed processing) or separately, where each control subsystem 108 is configured to handle specific aspects and/or functions, and/or to process data used to generate a model used only for a specific medical imaging system. In some implementations, the control subsystem 108 may be local (for example, in the same place as one or a plurality of X-ray imaging systems 100, such as in the same facility and/or the same local network). In other implementations, the control subsystem 108 may be remote and thus can only be accessed via a remote connection (for example, via the Internet or other available remote access technologies). In a specific implementation, the control subsystem 108 may be configured in a cloud-like manner, and may be accessed and/or used in a manner substantially similar to that of accessing and using other cloud-based systems.

In some embodiments, the system 100 further includes a computing device 120. The computing device 120 may be configured to use digitized signals to reconstruct one or a plurality of required images and/or determine useful diagnostic information corresponding to the object under examination 102, wherein the computing device 120 may include one or a plurality of dedicated processors, graphics processing units, digital signal processors, microcomputers, microcontrollers, application-specific integrated circuits (ASICs), field programmable gate array (FPGA) or other suitable processing devices.

In some embodiments, the system 100 further includes a storage device 122, where the computing device 120 may store the digitized signals in the storage device 122. For example, the storage device 122 may include a hard disk drive, a floppy disk drive, a CD-read/write (CD-R/W) drive, a digital versatile disc (DVD) drive, a flash drive, and/or a solid-state storage device. The storage device is configured to store a program executable by a computer, and when the computer executes the program, a plurality of components of the X-ray imaging system are enabled to implement operations corresponding to the aforementioned imaging sequence. When the computer executes the program, a medical imaging method may also be performed to post-process the original image to obtain an optimized image after post-processing.

Although FIG. 1 illustrates the storage device 122, the computing device 120, and the control subsystem 108 as separate devices, in some embodiments, one or a plurality of them may be combined into a single device to effectively utilize the floor space and/or meet expected imaging requirements.

In some embodiments, the system 100 further includes a display device 124. The display device 124 can be configured to display a reconstructed image and/or diagnostic information, etc.

In some embodiments, the system 100 further includes an operator workstation 126. The operator workstation 126 allows a user to receive and evaluate the reconstructed image, and input a control instruction (an operation signal or a control signal). The operator workstation 126 may include a user interface (or a user input device), such as a keyboard, a mouse, a voice activated controller, or any other suitable input devices in the form of an operator interface. An operator may input an operation signal/control signal, for example, one or a plurality of scan parameters, to the control subsystem 108 through the user interface and/or request required diagnostic information and/or image to evaluate the internal structure and/or functionality of the object under examination 102.

Figure 2:
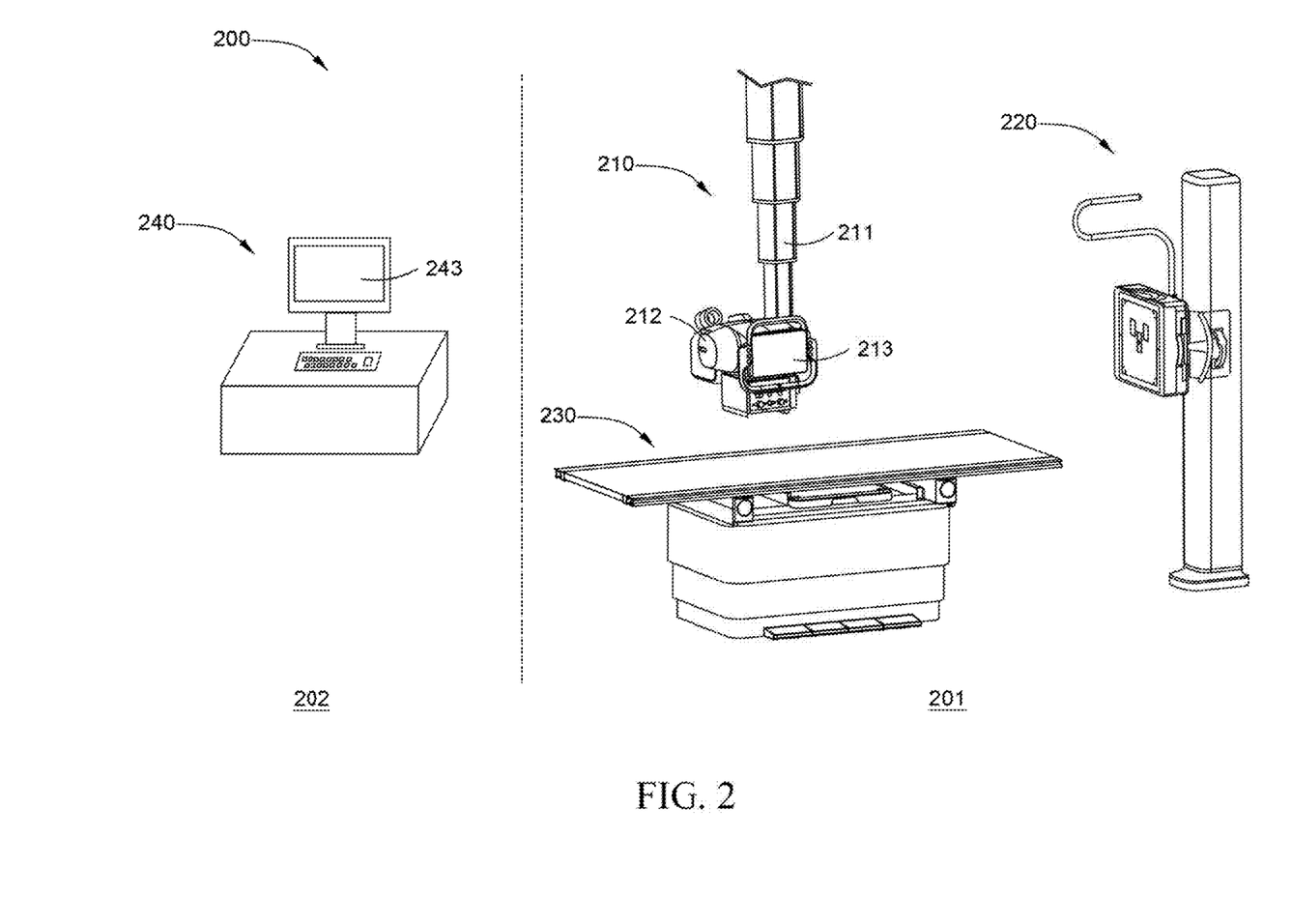
FIG. 2 is a schematic diagram of a suspended X-ray imaging system according to some embodiments of the present invention.

FIG. 2 is a schematic diagram of a suspended X-ray imaging system 200 according to some embodiments of the present invention. As shown in FIG. 2, the X-ray imaging system includes a telescopic overhead tube suspension (OTS) 210 for bulb tube, a wall stand 220, an examination bed 230 disposed in a scan room 201, and a console 240 disposed in a control room 202.

Specifically, the console 240 includes a first user module 243. The first user module 243 is configured to perform image processing on an acquired medical image. Specifically, the first user module 243 may include a display unit and/or a user interface and/or a printer, etc.

The medical image may be an image reconstructed from medical data sent by the detector, or may be an image stored in a hospital information system (HIS), a radiological information system (RIS), and/or a picture archive communication system (PACS).

For ease of display, a guide rail part of the telescopic overhead tube suspension 210 for bulb tube is omitted in FIG. 2. Specifically, in the scan room 201, the OTS 210 for bulb tube includes a telescopic cylinder 211, a bulb tube 212, and a second user module (console) 213. One end of the telescopic cylinder 211 is connected to the guide rail, another end is connected to the bulb tube 212, and the telescopic cylinder 211 is telescopic (or movable) in a vertical direction. A lower end of the telescopic cylinder 211 is provided with a rotating part, and the rotating part can drive the bulb tube 212 to rotate. The X-ray source is usually disposed in the bulb tube 212.

The second user module 213 may be configured to perform exposure setting. Specifically, the second user module 213 is installed on the bulb tube 212, and the second user module 213 includes user interfaces such as a display screen and a control button for performing exposure settings before exposure, such as at least one of selection in an object list, confirmation of object information, selection of a protocol, and positioning.

Generally, in addition to image processing the acquired medical image, the first user module can also be configured to perform exposure setting on the object under examination. However, since positioning and other operations all involve adjustment for the bulb tube and/or the detector in distance and/or angle as well as the position and/or posture of the object under examination, it is relatively inconvenient to use the first user module for positioning. Therefore, the second user module is usually used for exposure setting.

In some embodiments, the second user module may also be a portable controller, which may include a personal digital assistant (PDA), a palmtop computer, a laptop computer, a smart phone, a tablet computer such as an iPad™, or any suitable general-purpose or special-purpose portable interface device. The portable controller is configured to be held by the user and wirelessly communicate with the detector and/or X-ray source. The portable controller and the detector and/or X-ray source can utilize any suitable wireless communication protocol, such as an IEEE802.15.4 protocol, an ultra-wideband (UWB) communication standard, a Bluetooth communication standard, or any IEEE802.11 communication standard.

The wall stand 220 includes a first detector module, and the examination bed 230 includes a second detector module. The selection or use of the first detector module and the second detector module can be determined on the basis of an imaging site and/or an imaging protocol of the object to be examined, so as to carry out imaging examination in a lying or standing position.

In a complete exposure examination, firstly, information of the object to be examined needs to be obtained to obtain information such as the age, imaging site, etc. thereof, then an imaging protocol is automatically or manually determined or obtained on the basis of the information of the object to be examined to determine an imaging dose, imaging in a lying or standing position, etc., and positioning is performed on the basis of the imaging protocol to determine the distance between the X-ray source and the detector, the angle of the X-ray source, the height and angle of the detector in the wall stand, and the position and posture of the object under examination, etc. Then, after the aforementioned exposure settings are complete, exposure can be performed. Secondly, after the exposure is complete, the detector would send acquired medical data to the console 240 to process the medical data to obtain a medical image, and then image processing is performed on the medical image. Specifically, image post-processing is performed, for example, noise reduction and/or adjustment of the contrast, brightness, resolution, etc. of the image and/or adjustment of the size of the image and/or printing and saving the image, etc. Finally, after the image post-processing process is over or complete, the examination of the object under examination is complete.

Since the image post-processing is performed on the first user module in the control room while the scan room and the second user module are idle, by configuration of performing the exposure setting during the image post-processing, the imaging efficiency can be improved for saving time.

In some embodiments, the X-ray imaging system 200 further includes a control module (not shown in the figure), which can perform exposure setting of a next object via the second user module 213 during the image processing on the medical image data of the current object by the first user module 243. Specifically, the control module may be disposed in the console 240, or the control module may be integrated in the first user module.

In some embodiments, after the image processing process of the current object and the exposure setting of the next object are complete, at least one of the first user module 243 and the second user module 213 is further configured to perform an exposure operation.

Although it is defined in the present application that the next object can be exposed only after the image processing process of the current object is complete, those skilled in the art should understand that with the development of technology, it is also possible to perform exposure provided that the exposure setting is complete and the user has already left the scan room, and data obtained after the exposure can be stored in a temporary memory or other locations. When the first user module completes the image processing process of the previous object, the data saved in the temporary memory would be sent or synchronized to the first user module to continue image processing.

Figure 3:
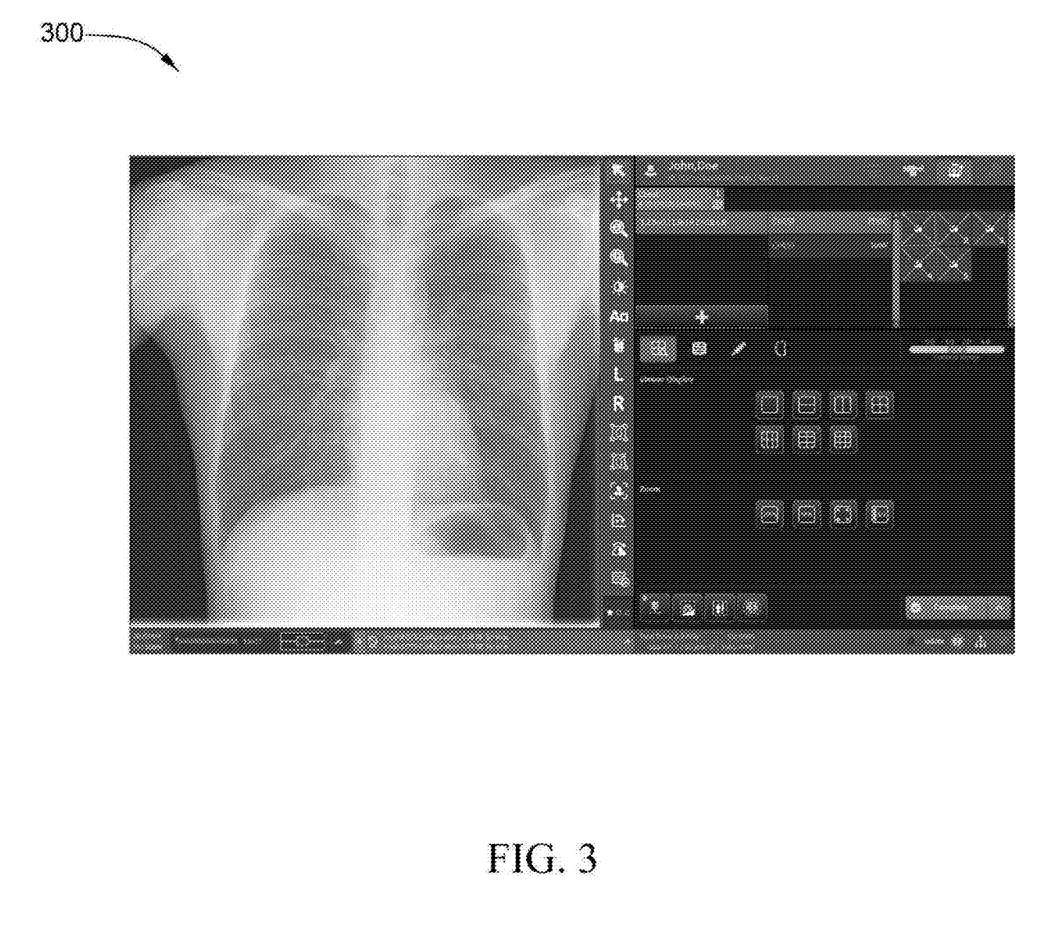
FIG. 3 is an image processing interface displayed by a first user module in the X-ray imaging system shown in FIG. 2.
Figure 4:
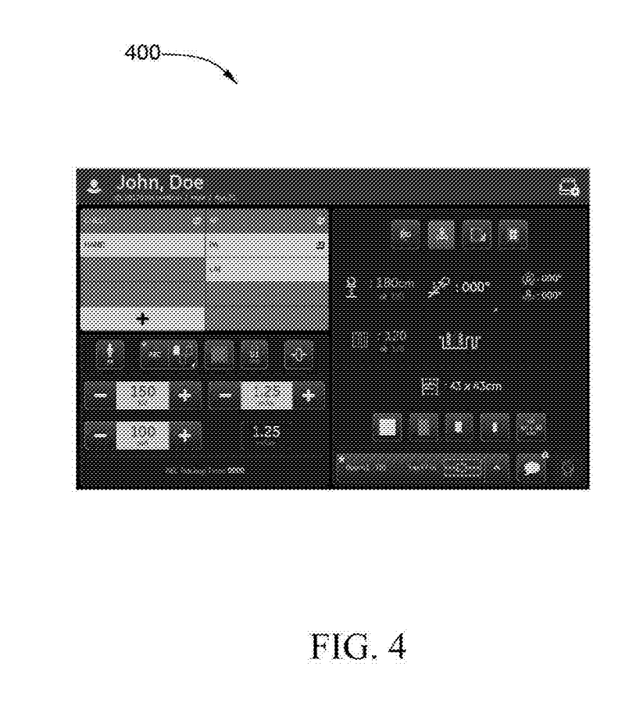
FIG. 4 is an exposure setting interface displayed by a second user module in the X-ray imaging system shown in FIG. 2.
Figure 5:
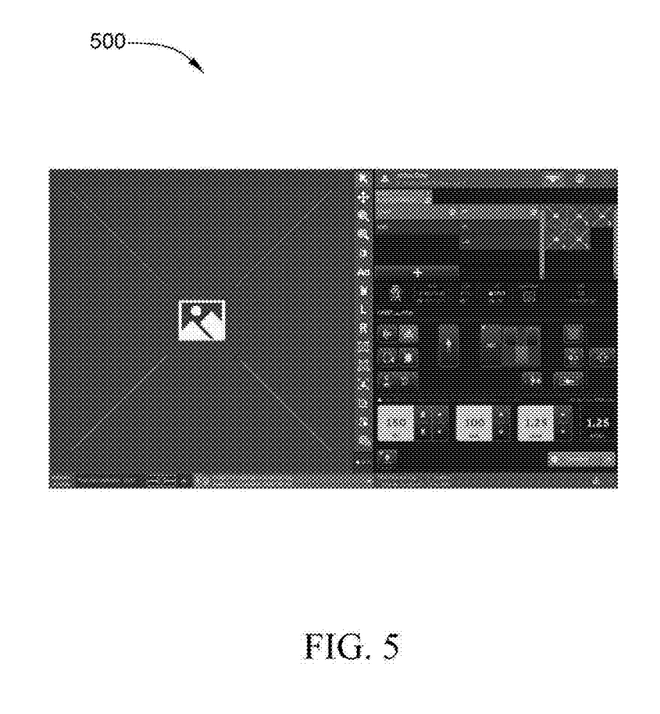
FIG. 5 is an exposure setting interface displayed by the first user module in the X-ray imaging system shown in FIG. 2.

FIG. 3 shows an image processing interface 300 displayed by the first user module in the X-ray imaging system shown in FIG. 2, FIG. 4 shows an exposure setting interface 400 displayed by the second user module in the X-ray imaging system shown in FIG. 2, and FIG. 5 shows an exposure setting interface 500 displayed by the first user module in the X-ray imaging system shown in FIG. 2. As shown in FIGS. 3-5, in some embodiments, the first user module comprises an interface 300 for displaying the image processing, the second user module comprises an interface 400 for the exposure setting, and the first user module is configured to synchronously display the interface 500 for the exposure setting of the next object displayed by the second user module when the image processing process of the current object ends.

Specifically, in the interface 300, the user can perform various image processing operations on the acquired image. In the interface 400, the user can perform exposure settings, such as an imaging voltage, current, source-to-image distance (SID), X-ray source angle, field of view (FOV), etc. After the first user module completes the image processing, printing and saving of the current object, the exposure setting interface as shown in FIG. 5 can be displayed, and various information and/or data of the exposure setting performed by the second user module can be automatically synchronized to the display interface 500. After the first user module completes the image processing, adjustment or modification of parameters and/or data performed by the second user module would also be synchronously displayed in the second user module, in which case the first user module and the second user module are equivalently in a continuous screen mode.

Although proposed in the present application is that the exposure setting data can be automatically synchronized after the image processing is complete, those skilled in the art should understand that the data of the exposure setting performed in the second user module can be saved in a memory, and the exposure setting data can be manually synchronized to the first user module by providing a manual synchronization option in the display interface 500. In order to further ensure the integrity and accuracy of the data and avoid data loss situations due to data transmission errors or system power-off or failures, it is also possible to still manually synchronize the exposure setting data after automatic synchronization.

The display interfaces in FIGS. 3-5 are only schematically shown and do not involve main points of protection of the present application, and therefore should not limit the scope of protection of the present application.

Figure 6:
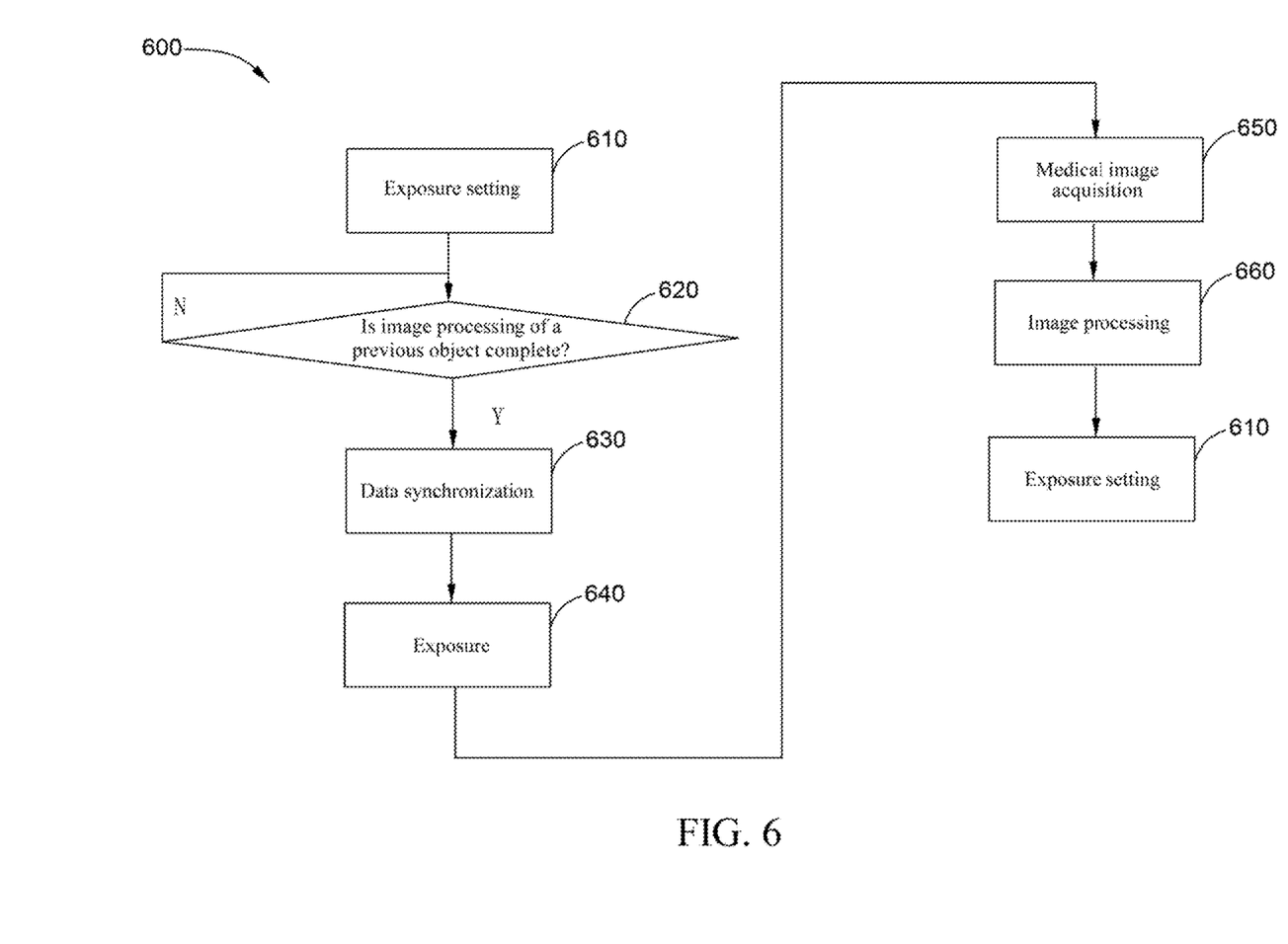
FIG. 6 is a schematic diagram of a work flow of a control module in some embodiments shown in FIG. 2.

FIG. 6 shows a schematic diagram of a work flow of the control module shown in FIG. 2. As shown in FIG. 6, using a check list of objects A, B, and C to be examined as an example, for object A to be examined, exposure setting is first performed via the second user module (610), and then it is determined whether the first user module is still performing image processing (620). If the image processing process is still in progress, waiting until the first user module ends the image processing process, and then exposure setting data of the second user module is synchronized to the first user module (630). When the exposure setting is complete and the image processing is not performed, an exposure operation (640) can be performed on object A, and a medical image of object A can be obtained (650) by processing and reconstructing data acquired by the detector module, and image processing is performed on the medical image (660). During the image processing, the second user module is used to perform exposure setting on object B to be examined, and then steps 620 to 660 are repeated.

Figure 7:
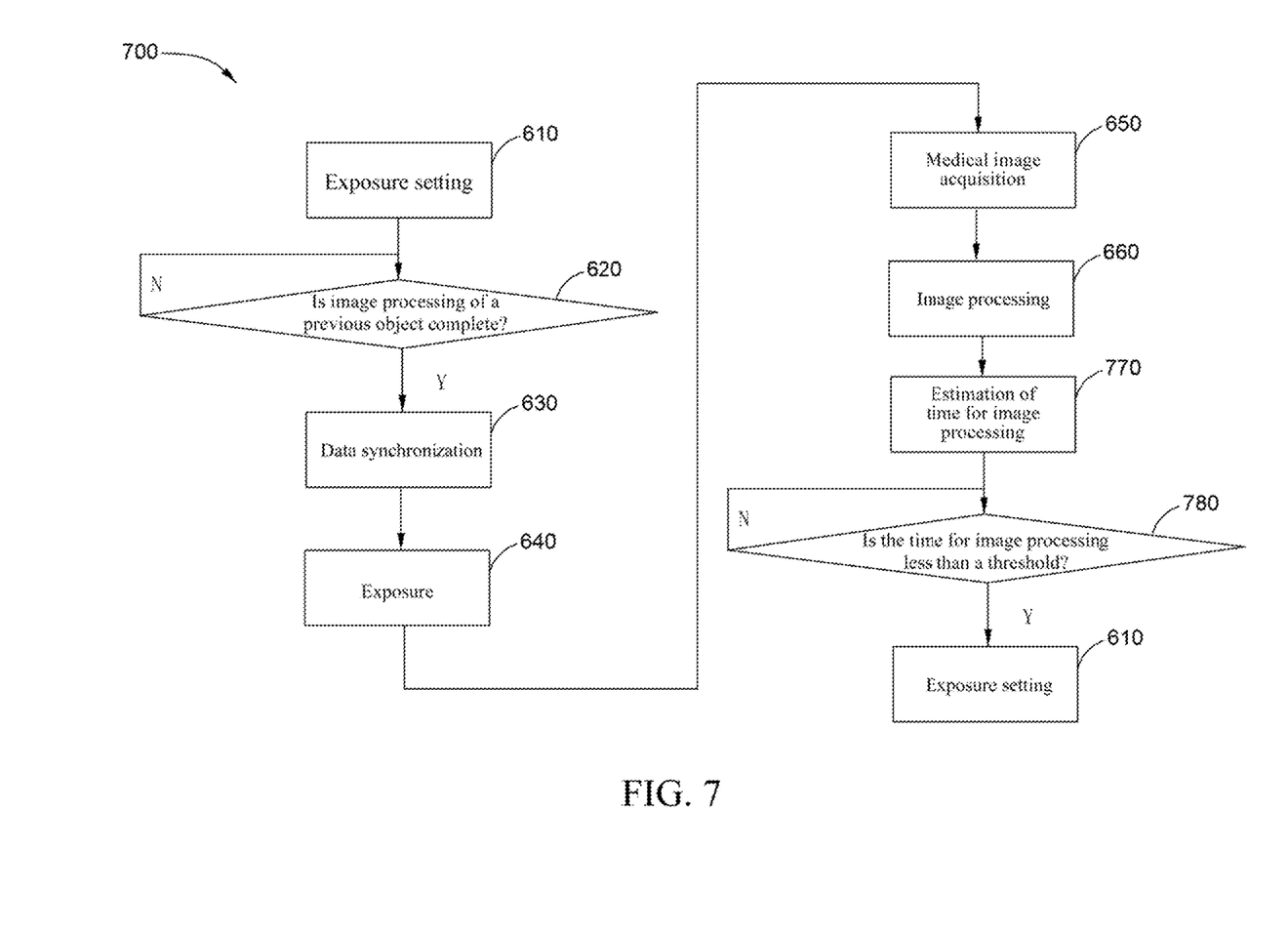
FIG. 7 is a schematic diagram of a work flow of a control module in some other embodiments shown in FIG. 2.

FIG. 7 shows a schematic diagram of a work flow of the control module according to some other embodiments of the present invention. As shown in FIG. 7, the control module can perform, during image processing on medical image data of a current object by the first user module 243, exposure setting of a next object via the second user module 213 on the basis of estimated time required for the image processing.

Generally, for an X-ray imaging system, time required for image post-processing is almost the same as time required for exposure setting. Therefore, when exposure of the current object is complete and image processing is started, exposure setting can be performed on the next object. Certainly, in some embodiments, the time for image post-processing often exceeds the time for exposure setting, for example, for some imaging that requires image reconstruction or imaging that uses simple exposure settings. Therefore, the control module can estimate the time required for the image processing (process 770), and perform the exposure setting of the next object on the basis of the time.

Specifically, the control module can estimate the required time on the basis of an imaging protocol of the current object. For example, the time required for the image processing may be estimated according to the imaging type, image stitching imaging, helical tomography (TOMO) imaging, dual energy imaging, etc., or the time required for the image processing may be estimated according to different needs such as an imaging site or a disease type corresponding thereto, or the time required for the image processing may be estimated on the basis of the number of images to be processed or printed, etc., or estimated on the basis of other parameters in the imaging. The estimated time can be saved in the X-ray imaging system in the form of a lookup table or cloud storage or the like.

Those skilled in the art should understand that the time required for the image processing may also be obtained through manual estimation by the user (or technician).

Specifically, when the time required for the image processing is less than a first threshold, the exposure setting of the next object is performed via the second user module 213. Specifically, the first threshold is confirmed on the basis of the time required for the exposure setting. Through such settings, it is possible to avoid the situation in which after positioning is complete, the object under examination needs to wait for the image processing of the previous object to be complete so that exposure can be performed, which deteriorates the user experience and may also cause deviations such as a shift of a region of interest due to movement of the object under examination. The first threshold may not be a determined time value, but can be judged or determined according to experience of the user. For example, when printing of an image is started, it is considered that the time required for the image processing is substantially less than the first threshold, and then the exposure setting for the next object can be performed in parallel.

In some embodiments, the control module is further configured to generate an instruction signal to stop examination of a subsequent object on the basis of the time required for the image processing. Specifically, when the time required for the image processing is greater than a second threshold, an instruction signal is generated to stop examination of a subsequent object. Further, when the object requires TOMO imaging, it takes a very long time to complete post-processing of an acquired image, and the control module can switch the system to a background mode, and no longer perform imaging examination on a following object, and suspend subsequent exposure settings. Certainly, the control module may also send an instruction signal to prompt the user to assign the following object in the examination list to another scan rooms, etc. Certainly, the control module may also select an object that requires long positioning time as a next object and perform exposure setting thereon.

The control module may further select the next object in an object list on the basis of an imaging protocol of each object according to the estimated time required for the image processing. Specifically, the control module may sort the object list in order on the basis of the time required for the image processing and the imaging protocols of the objects in the object list to determine the next imaging object.

For example, when the current object is under TOMO examination, time for image processing thereof would be long. In this case, an object that requires long positioning time can be selected as the next object for exposure setting. Alternatively, when the current object merely is under regular imaging, and the next object in the object list is an object in an inconvenient situation who has just received an operation, the priority of the object can be moved backward, or the object can be arranged in another scan room, etc.

Certainly, the sorting of the object list may also be performed before daily imaging. Before the start of one day's imaging or after a new object under examination is added to the object list, the control module can perform sorting thereon on the basis of various parameters of the object, which may include factors such as an imaging site, emergency or outpatient service, and inconvenient situation or not. In some embodiments, the sorting may be obtained on the basis of a sorting model obtained by deep learning network training.

Figure 8:
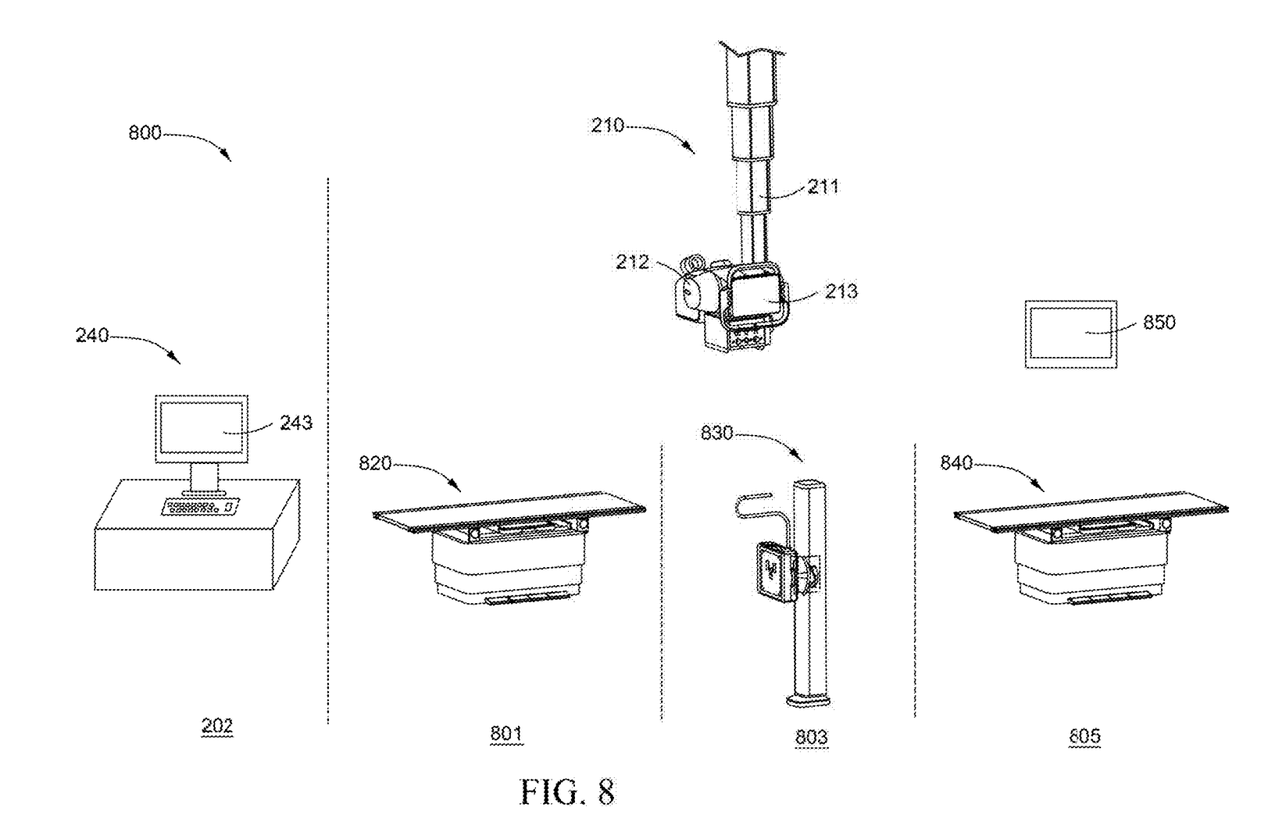
FIG. 8 is a schematic diagram of an X-ray imaging system according to still some embodiments of the present invention.

FIG. 8 shows a schematic diagram of an X-ray imaging system 800 according to still some embodiments of the present invention. As shown in FIG. 8, different from the X-ray imaging system 200 shown in FIG. 2, the X-ray imaging system 800 includes a plurality of scan rooms, for example, a first scan room 801, a second scan room 803, and a third scan room 805, and the first scan room 801 includes a first scanner bed 820 therein, the second scan room 803 includes a wall stand 830 therein, and the third scan room 805 includes a second scanner bed 830 therein.

In other embodiments, time for exposure setting may exceed time for image post-processing. For example, an object under examination cannot be conventionally positioned due to inconvenient situation, etc. In this case, a control module can perform exposure setting on different objects via at least one second user module during image processing of medical image data of a current object by a first user module. Specifically, when the X-ray imaging system includes one second user module, i.e., a control device 213 disposed on a bulb tube, different objects are arranged in different scan rooms by switching viewing of imaging protocols in an object list, etc., and the objects under examination are respectively positioned, and other exposure settings are performed before exposure. When the X-ray imaging system includes a plurality of second user modules, for example, the control device 213 disposed on the bulb tube and one or a plurality of portable controllers, different second user modules can be used to respectively perform exposure settings on different objects under examination.

Although three scan rooms with different configurations are shown in FIG. 8, those skilled in the art can understand that any number of scan rooms can be configured, and different detectors in the form of examination beds and/or wall stands for standing and/or lying positions can be configured in the scan rooms, so as to meet actual imaging needs.

The medical imaging system in the present application may be a fixed X-ray imaging system as shown in FIG. 2 or FIG. 8, or may be a mobile X-ray imaging system, and the second user module may be a user interface such as a portable mobile tablet or the like.

Figure 9:
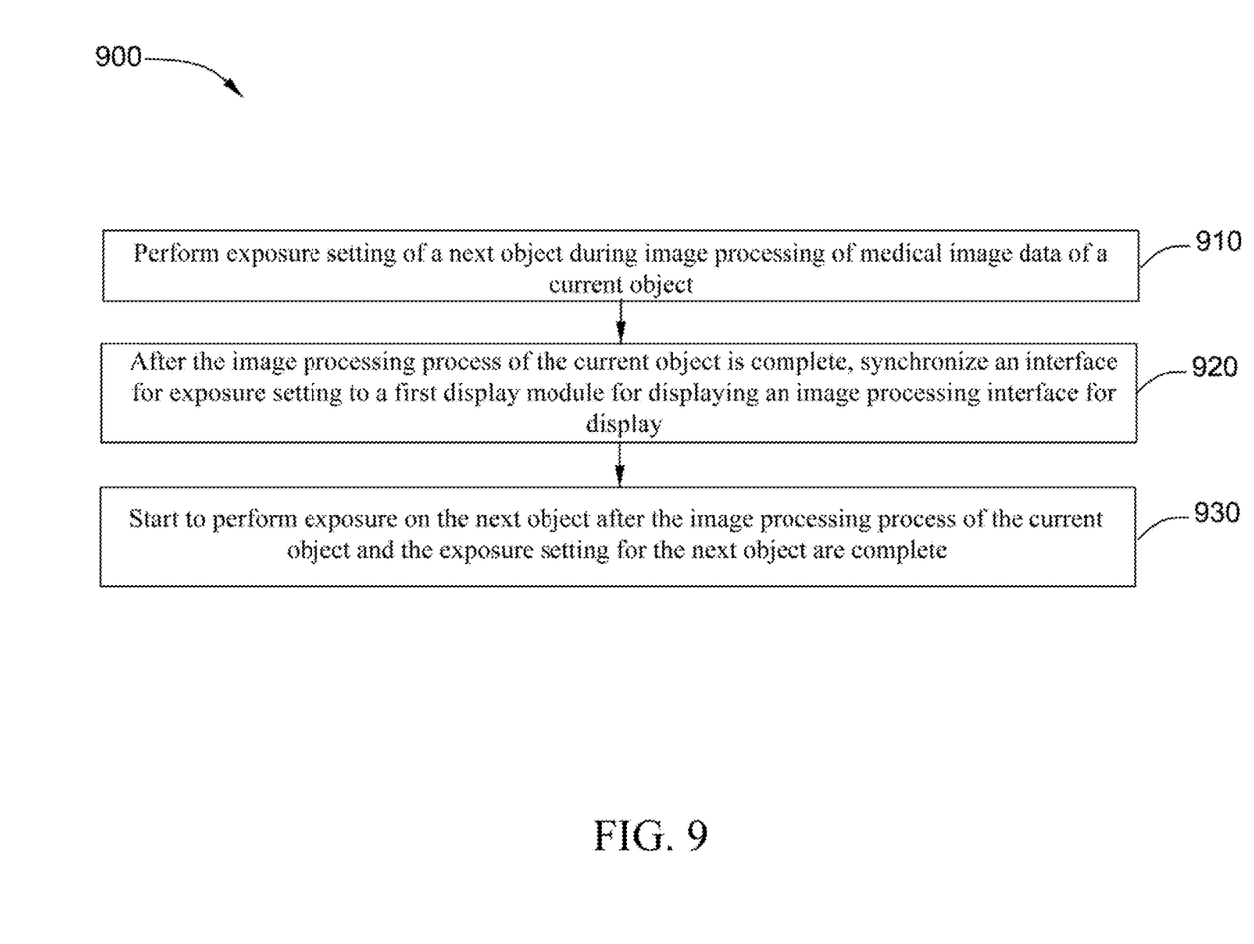
FIG. 9 is a flowchart of an operating method of a medical imaging system according to some embodiments of the present invention.

FIG. 9 shows a flowchart of an operating method 900 of a medical imaging system according to some embodiments of the present invention. As shown in FIG. 9, the operating method 900 of a medical imaging system includes step 910.

In step 910, exposure setting of a next object is performed during image processing of medical image data of a current object.

Specifically, the exposure setting comprises at least one of selection in an object list, confirmation of object information, selection of a protocol, and positioning. The positioning includes adjustment of the distance and angle of an X-ray source and/or a detector, as well as adjustment of the position and/or posture of an object under examination, etc.

In some embodiments, performing the image processing on the medical image data of the current object comprises displaying an interface for the image processing by a first display module, and the exposure setting of the next object comprises displaying an interface for the exposure setting by a second display module. The operating method 900 of a medical imaging system further includes step 920.

In step 920, after the image processing process of the current object is complete, the interface for the exposure setting is synchronized to the first display module for display. In some embodiments, data in the interface for the exposure setting can be automatically synchronized to the first display module. In some other embodiments, the data in the exposure setting can be manually synchronized to the first display module by storing the data in a memory.

In some embodiments, the operating method 900 of a medical imaging system further includes step 930.

In step 930, after the image processing process of the current object and the exposure setting for the next object are complete, exposure performed on the next object is started.

Figure 10:
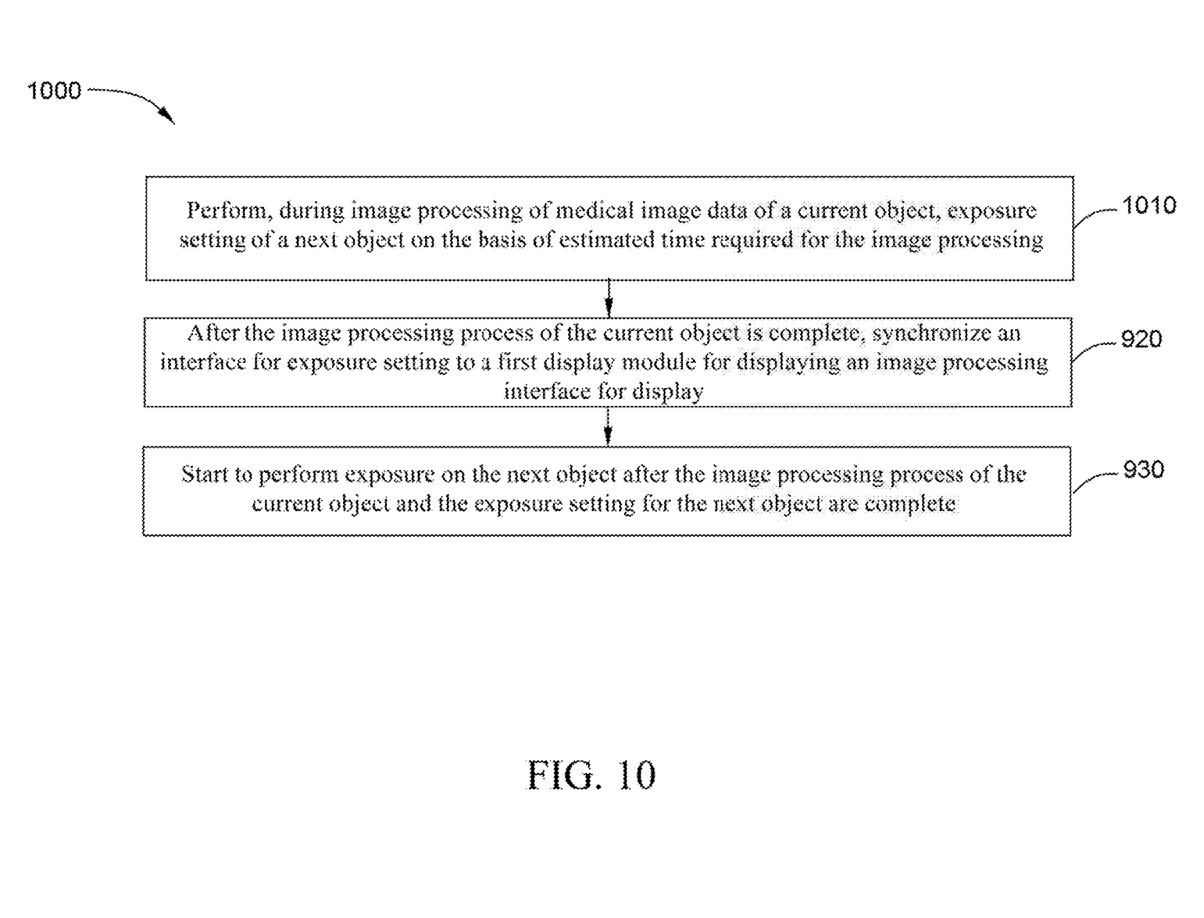
FIG. 10 is a flowchart of an operating method of a medical imaging system according to some other embodiments of the present invention.

FIG. 10 shows a flowchart of an operating method 1000 of a medical imaging system according to some other embodiments of the present invention. Different from the operating method 900 shown in FIG. 9, the operating method shown in FIG. 10 includes step 1010.

In step 1010, during image processing of medical image data of a current object, exposure setting of a next object is performed on the basis of estimated time required for the image processing.

Specifically, estimating the time required for the image processing comprises estimating the required time on the basis of an imaging protocol of the current object. For example, the time required for the image processing may be estimated according to the imaging type, image stitching imaging, TOMO imaging, dual energy imaging, etc., or the time required for the image processing may be estimated according to different needs such as an imaging site or a disease type corresponding thereto, or the time required for the image processing may be estimated on the basis of the number of images to be processed or printed, etc., or estimated on the basis of other parameters in the imaging. The estimated time can be saved in the X-ray imaging system in the form of a lookup table or cloud storage or the like.

Specifically, when the time required for the image processing is less than a first threshold, the exposure setting of the next object is performed. Specifically, the first threshold is confirmed on the basis of time required for the exposure setting. The first threshold may not be a determined time value, but can be judged or determined according to experience of the user. For example, when printing of an image is started, it is considered that the time required for the image processing is substantially less than the first threshold, and then the exposure setting for the next object can be performed in parallel.

Specifically, when the time required for the image processing is greater than a second threshold, an instruction signal is generated to stop examination of a subsequent object. For example, when the object requires TOMO imaging, it takes a very long time to complete post-processing of an acquired image, and the control module can switch the system to a background mode, and no longer perform imaging examination on a following object, and suspend subsequent exposure settings.

Specifically, before the performing exposure setting of a next object, the method can further comprise: selecting the next object in an object list on the basis of an imaging protocol of each object according to the estimated time required for the image processing.

Although the operating method of a medical imaging system in some embodiments of the present invention is mainly described by using an X-ray imaging system as an example, those skilled in the art should understand that the operating method is not limited to application to the X-ray imaging system, but can also be applied to a computer tomography system or a magnetic resonance imaging system. Specifically, in the magnetic resonance imaging system, settings before image acquisition of writing an object, such as determination of a scan sequence, a pre-scan, determination of a region of interest, and the like, are mainly performed during image processing of medical image data of a current object.

In the operating method of a medical imaging system in some embodiments of the present invention, by continuing to perform exposure setting of a next object in parallel during continued image processing of a medical image, it is possible to shorten waiting time of an object to be examined and improve the examination efficiency. Moreover, by starting the exposure setting by estimating time for the image processing, it is possible to avoid long waiting time of the object to be examined after positioning and consequently inaccurate positioning due to movement, etc., thereby improving user experience and avoiding repeated positioning. By configuring a plurality of scan rooms, it is possible to save exposure setting time of the object under examination for which positioning is time-consuming due to inconvenient situation.

The present invention may further provide a non-transitory computer-readable storage medium for storing an instruction set and/or a computer program. When executed by a computer, the instruction set and/or computer program causes the computer to perform the aforementioned medical imaging method. The computer executing the instruction set and/or computer program may be a computer of an X-ray imaging system, or may be other devices/modules of the X-ray imaging system. In one embodiment, the instruction set and/or computer program may be programmed into a processor/controller of the computer.

Specifically, when executed by the computer, the instruction set and/or computer program causes the computer to: perform exposure setting of a next object during image processing of medical image data of a current object.

The instruction set may include various commands that instruct a computer acting as a processor or instruct a processor to perform particular operations, such as the methods and processes of various embodiments. The instruction set may be in the form of a software program, and the software program can form part of one or a plurality of tangible, non-transitory computer-readable media. The software may be in various forms such as system software or application software. In addition, the software may be in the form of a set of independent programs or modules, a program module within a larger program, or part of a program module. The software may also include modular programming in the form of object-oriented programming. The input data may be processed by the processor in response to an operator command, or in response to a previous processing result, or in response to a request made by another processor.

As used herein, the term "computer" may include any processor-based or microprocessor-based system including a system that uses a microcontroller, a reduced instruction set computer (RISC), an application specific integrated circuit (ASIC), a logic circuit, and any other circuit or processor capable of executing the functions described herein. The above examples are merely exemplary and thus are not intended to limit the definition and/or meaning of the term "computer" in any manner.

Some exemplary embodiments have been described above; however, it should be understood that various modifications can be made. For example, if the described techniques are performed in a different order and/or if the components of the described system, architecture, device, or circuit are combined in other manners and/or replaced or supplemented with additional components or equivalents thereof, a suitable result can be achieved. Accordingly, other implementations also fall within the protection scope of the claims.

The invention claimed is:

1. An operating method of a medical imaging system, comprising:
 performing exposure setting of a next object during image processing of medical image data of a current object; and
 synchronously displaying an interface for the exposure setting of the next object displayed by a user module when the image processing process of the current object ends,
 wherein exposure setting includes altering an imaging voltage, current, source-to- image distance (SID), X-ray source angle, or field of view (FOV).

2. The operating method according to claim 1, wherein the performing exposure setting of a next object comprises performing the exposure setting of the next object on the basis of estimated time required for the image processing.

3. The operating method according to claim 2, wherein estimating the time required for the image processing comprises estimating the required time on the basis of an imaging protocol of the current object.

4. The operating method according to claim 2, wherein when the time required for the image processing is less than a first threshold, the exposure setting of the next object is performed.

5. The operating method according to claim 2, wherein when the time required for the image processing is greater than a second threshold, an instruction signal is generated to stop examination of a subsequent object.

6. The operating method according to claim 2, wherein before the performing exposure setting of a next object, the method further comprises:
 selecting the next object in an object list on the basis of an imaging protocol of each object according to the estimated time required for the image processing.

7. The operating method according to claim 1, further comprising: starting to perform exposure on the next object after the image processing process of the current object and the exposure setting for the next object are complete.

8. The operating method according to claim 1, wherein performing the image processing on the medical image data of the current object comprises displaying an interface for the image processing by a first display module, and the exposure setting of the next object comprises displaying an interface for the exposure setting by a second display module, and the operating method further comprises:
 after the image processing process of the current object is complete, synchronizing the interface for the exposure setting to the first display module for display.

9. The operating method according to claim 1, wherein the exposure setting comprises at least one of selection in an object list, confirmation of object information, selection of a protocol, and positioning.

10. A non-transitory computer-readable storage medium for storing a computer program, wherein when executed by a computer, the computer program causes the computer to perform the operating method according to claim 1.

11. An X-ray imaging system, comprising:
 a telescopic overhead suspension;
 a console;
 a first user module included within the console, configured to perform image processing on an acquired medical image;
 a second user module coupled to the telescopic overhead suspension, configured to perform exposure setting; and
 a control module, configured to perform exposure setting of a next object via the second user module during image processing of medical image data of a current object by the first user module,
 wherein the control module synchronously displays an interface for the exposure setting of the next object displayed by the second user module when the first user module completes image processing of the current object.

12. An X-ray imaging system according to claim 11, wherein the first user module is located in a control room, and the second user module is located in a scan room.

13. An X-ray imaging system according to claim 11, wherein the first user module comprises an interface for displaying the image processing, the second user module comprises an interface for the exposure setting, and the first user module is configured to synchronously display the interface for the exposure setting of the next object displayed by the second user module when the image processing process of the current object ends.

14. An X-ray imaging system according to claim 11, wherein at least one of the first user module and the second user module is further configured to perform an exposure operation after the image processing process of the current object and the exposure setting of the next object are complete.

15. An X-ray imaging system according to claim 11, wherein the control module is further configured to perform, during the image processing of the medical image data of the current object by the first user module, the exposure setting of the next object via the second user module on the basis of estimated time required for the image processing.

16. An X-ray imaging system according to claim 15, wherein the control module is further configured to generate an instruction signal to stop examination of a subsequent object on the basis of the time required for the image processing.

* * * * *